(12) United States Patent
Carlyon

(10) Patent No.: US 8,708,969 B2
(45) Date of Patent: Apr. 29, 2014

(54) SAFETY DEVICE ACTUATION SYSTEM

(75) Inventor: James L. Carlyon, Farmington, MO (US)

(73) Assignee: Covidien LP, Mansfield, MA (US)

( * ) Notice: Subject to any disclaimer, the term of this patent is extended or adjusted under 35 U.S.C. 154(b) by 1329 days.

(21) Appl. No.: 12/489,535

(22) Filed: Jun. 23, 2009

(65) Prior Publication Data

US 2009/0326476 A1    Dec. 31, 2009

Related U.S. Application Data

(60) Provisional application No. 61/076,863, filed on Jun. 30, 2008.

(51) Int. Cl.
*A61M 5/32* (2006.01)
*A61M 5/178* (2006.01)

(52) U.S. Cl.
USPC ....... 604/198; 604/192; 604/163; 604/164.08

(58) Field of Classification Search
USPC ................................... 604/197, 163; 128/919
See application file for complete search history.

(56) References Cited

U.S. PATENT DOCUMENTS

| | | | |
|---|---|---|---|
| 4,795,432 A * | 1/1989 | Karczmer | 604/110 |
| 4,813,426 A | 3/1989 | Haber et al. | |
| 4,900,311 A | 2/1990 | Stern et al. | |
| 4,973,316 A | 11/1990 | Dysarz | |
| 5,007,901 A | 4/1991 | Shields | |
| 5,084,030 A | 1/1992 | Byrne et al. | |
| 5,106,379 A * | 4/1992 | Leap | 604/198 |
| 5,232,456 A | 8/1993 | Gonzalez | |
| 5,360,408 A | 11/1994 | Vaillancourt | |
| 5,368,568 A | 11/1994 | Pitts et al. | |
| 5,480,388 A | 1/1996 | Zadini et al. | |
| 5,501,675 A | 3/1996 | Erskine | |
| 5,591,138 A | 1/1997 | Vaillancourt | |
| 5,928,199 A | 7/1999 | Nakagami | |
| 6,010,487 A | 1/2000 | DeMichele et al. | |

(Continued)

FOREIGN PATENT DOCUMENTS

| EP | 1258263 A1 | 11/2002 |
|---|---|---|
| WO | WO00/47256 | 8/2000 |

(Continued)

OTHER PUBLICATIONS

European Search Report mailed Dec. 18, 2009 in counterpart EP Application No. EP09163662.1 filed Jun. 24, 2009.

*Primary Examiner* — Manuel Mendez
*Assistant Examiner* — Weng Lee
(74) *Attorney, Agent, or Firm* — Lisa E. Winsor, Esq.

(57) ABSTRACT

The present disclosure relates to a safety needle assembly that includes a syringe and a safety mechanism. The safety mechanism includes a housing defining an internal cavity, a shield member at least partially disposed within the internal cavity, and first and second locking members that are configured to selectively engage and maintain the shield member in one or more predetermined positions. The locking members are movable between a locked position, in which the locking members are in engagement with the shield member to substantially prevent axial movement thereof, and a release position, in which the locking members are disengaged from the shield member to permit axial movement thereof. The first and second locking members each include biasing members. The biasing member of the each locking member is positioned to cooperate with the other locking member to normally bias the locking members towards the locked position.

28 Claims, 13 Drawing Sheets

(56) References Cited

U.S. PATENT DOCUMENTS

| | | |
|---|---|---|
| 6,096,005 A | 8/2000 | Botich et al. |
| 6,171,284 B1 * | 1/2001 | Kao et al. ............ 604/192 |
| 6,210,371 B1 | 4/2001 | Shaw |
| 6,773,419 B2 | 8/2004 | Crawford et al. |
| 6,786,875 B2 | 9/2004 | Barker et al. |
| 6,860,872 B2 | 3/2005 | Teichert |
| 6,976,976 B2 | 12/2005 | Doyle |
| 7,037,292 B2 | 5/2006 | Carlyon et al. |
| 2002/0156426 A1 * | 10/2002 | Gagnieux et al. ............ 604/197 |
| 2007/0066937 A1 | 3/2007 | Jones et al. |

FOREIGN PATENT DOCUMENTS

| | | |
|---|---|---|
| WO | WO 2004/060445 A2 | 7/2004 |
| WO | WO 2005/079441 A2 | 9/2005 |
| WO | WO 2009/114762 A1 | 9/2009 |

* cited by examiner

SAFETY DEVICE ACTUATION SYSTEM

CROSS-REFERENCE TO RELATED APPLICATIONS

This application claims the benefit of U.S. Provisional Application No. 61/076,863, filed on Jun. 30, 2008.

BACKGROUND

1. Technical Field

The present disclosure relates generally to safety devices, and methods of using and manufacturing the same. More particularly, the present disclosure relates to a safety device with a mechanism that is selectively actuable to prevent hazardous exposure and/or inadvertent contact with a sharp element.

2. Background of the Related Art

Needles, such as hypodermic needles, for example, are used in a variety of applications, both medical and non-medial in nature, including medical and veterinary procedures, clinical research, and biotechnological, chemical, and pharmaceutical applications.

Cross-contamination and infection through inadvertent needle sticks have resulted in the development of a wide variety of safety needles used in the areas of I.V. therapy, venipuncture, phlebotomy, and syringes. However, known safety needles can often be difficult to use and manufacture, and can result in uncontrolled manipulation and/or faulty operation, thus frustrating their intended purpose.

SUMMARY

In one aspect, the present disclosure relates to a safety device assembly that includes a medical device having a sharp element and a safety mechanism that is positioned at a distal end of the medical device in association with the sharp element. The safety mechanism includes a housing defining an internal cavity, a shield member at least partially disposed within the internal cavity, and first and second locking members.

The first and second locking members are configured to selectively engage the shield member to maintain the shield member in one or more predetermined positions. The first and second locking members are movable between a locked position, in which the first and second locking members are in engagement with the shield member to substantially prevent axial movement thereof, and a release position, in which the first and second locking members are disengaged from the shield member to permit axial movement of the shield member to cover the sharp element. The first and second locking members each include a biasing member, and the biasing member of each locking member is positioned to cooperate with the other of the first and second locking members to normally bias the locking members towards the locked position.

In another aspect of the present disclosure, a safety needle assembly is described that includes a syringe and a safety mechanism positioned at a distal end of the syringe. The safety mechanism includes a housing defining an internal cavity, a shield member at least partially disposed within the internal cavity, and first and second locking members. In one embodiment of the safety mechanism, the first and second locking members may be substantially identical in configuration and dimensions.

The first and second locking members are configured and dimensioned to selectively engage the shield member to maintain the shield member in one or more predetermined positions, and are movable between a locked position and a release position. In one embodiment, the first and second locking members are adapted for reciprocal movement between the locked position and the release position.

In the locked position, the first and second locking members are in engagement with the shield member to substantially prevent axial movement thereof, and in the release position, the first and second locking members are disengaged from the shield member to permit axial movement thereof. The first and second locking members each include biasing members. The biasing member of the each locking member is positioned to cooperate with the other locking member to normally bias the locking members towards the locked position. In one embodiment of the safety mechanism, the biasing members of the first and second locking members respectively include first and second resilient fingers. In this embodiment, the first and second locking members further include first and second stops, respectively. The first resilient finger is configured and dimensioned for engagement with the second stop, and the second resilient finger is configured and dimensioned for engagement with the first stop to normally bias the first and second locking members towards the locked position.

In another embodiment, the first and second locking members may each include a tactile member configured for manual engagement to facilitate movement of the first and second locking members from the locked position to the release position.

The shield member is movable between retracted and advanced positions. In one embodiment, the safety needle assembly further includes a needle extending distally from the syringe. In this embodiment, when the shield member is in the retracted position, a distal end of the needle extends distally beyond a distal end of the shield member, and when the shield member is in an advanced position, the distal end of the shield member extends distally beyond the distal end of the needle. The safety needle assembly may further include a biasing member connected to the shield member to normally bias the shield member towards either the advanced position or the retracted position. As the shield member moves between the retracted and advanced positions, the shield member passes through the first and second locking members and an opening at a distal end of the housing.

The first locking member includes a first detent and the second locking member includes a second detent. In one embodiment, the first and second detents are receivable by at least one aperture formed in the shield member. When the first and second locking members are in the locked position, the first and second detents are positioned within the at least one aperture, and when the first and second locking members are in the release position, the first and second detents are displaced from the at least one aperture. As the first and second locking members move from the locked position to the release position, the first and second locking members are displaced radially inward with respect to a longitudinal axis of the housing.

In one embodiment, the at least one aperture includes a proximal pair of apertures and a distal pair of apertures. In this embodiment, the first and second detents are positionable within the distal pair of apertures to maintain the retracted position of the shield member, and are positionable within the proximal pair of apertures to maintain the advanced position of the shield member. The first detent is positioned on a first arm of the first locking member and the second detent is positioned on a second arm of the second locking member such that the first and second detents are displaced radially outward and out of engagement with the at least one aperture as the first and second locking members are displaced radially inward, thereby permitting the shield member to move from the retracted position to the advanced position.

In an alternate embodiment, the retracted position of the shield member is maintained through engagement of the distal end of the shield member with the first detent, and the advanced position of the shield member is maintained through engagement of a proximal end of the shield member with the second detent.

In another aspect of the present disclosure, a safety mechanism is disclosed that is adapted for use with a medical device. The safety mechanism includes a housing defining an internal cavity, a shield member at least partially disposed within the internal cavity, and first and second locking members.

The first and second locking members are configured and dimensioned to selectively engage the shield member to maintain the shield member in one or more predetermined positions, and are movable between a locked position and a release position. In the locked position, the first and second locking members are in engagement with the shield member to substantially prevent axial movement thereof, and in the release position, the first and second locking members are disengaged from the shield member to permit axial movement thereof. The first and second locking members each include a biasing member, the biasing member of each locking member being positioned to cooperate with the other of the first and second locking members to normally bias the locking members towards the locked position.

In another aspect of the present disclosure, a method of manufacturing a safety mechanism for use with a needle assembly is disclosed. The method includes the steps of providing a housing, a shield member, a biasing member, a first locking member, and a second locking member, positioning the biasing member and the shield member within the housing, and positioning the first and second locking members within the housing such that the first and second locking members maintain the shield member in a retracted position. The first and second locking members define substantially identical configurations and dimensions, and are positioned within the housing such that one of the first and second locking members is in an inverted position.

BRIEF DESCRIPTION OF THE DRAWINGS

Various embodiments of the present disclosure are described herein below with reference to the drawings, wherein.

DETAILED DESCRIPTION

Figure 1:
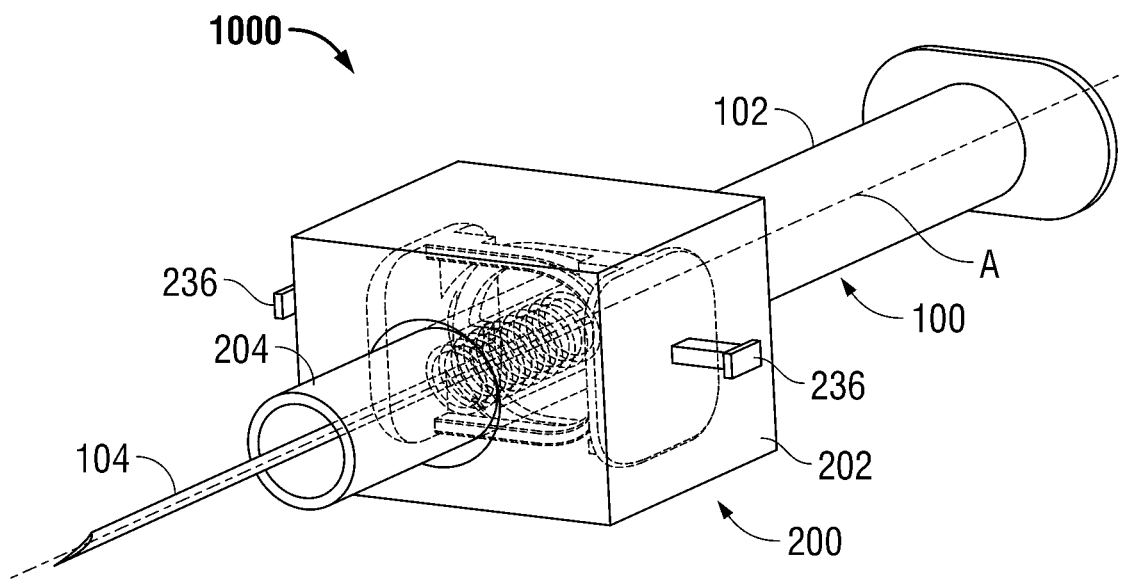
FIG. 1 is a side, perspective view of a safety needle incorporating a needle assembly and one embodiment of a safety mechanism that includes a housing, a shield member, a biasing member, and a pair of locking members in accordance with the present disclosure.

In the drawings and in the description which follows, in which like references characters identify similar or identical elements, the term "proximal" should be understood as referring to the end of an apparatus, or any component thereof that is closest to a practitioner during use, while the term "distal" should be understood as referring to the end that is furthest from the practitioner during use.

FIG. 1 illustrates a safety needle 1000 including a needle assembly 100 and one embodiment of a safety mechanism for use therewith, referred to generally by reference character 200, in accordance with the principles of the present disclosure. The needle assembly 100 extends along a longitudinal axis "A" and includes a syringe 102 and a needle 104. In alternative embodiments, the needle 104 may be configured as a scalpel blade, stylet, lancet, etc. The syringe 102 and the needle 104 may be fixedly attached or releasably coupled together using, for example, a luer-type connector, such that the needle 104 may be removed after use.

Figure 2:
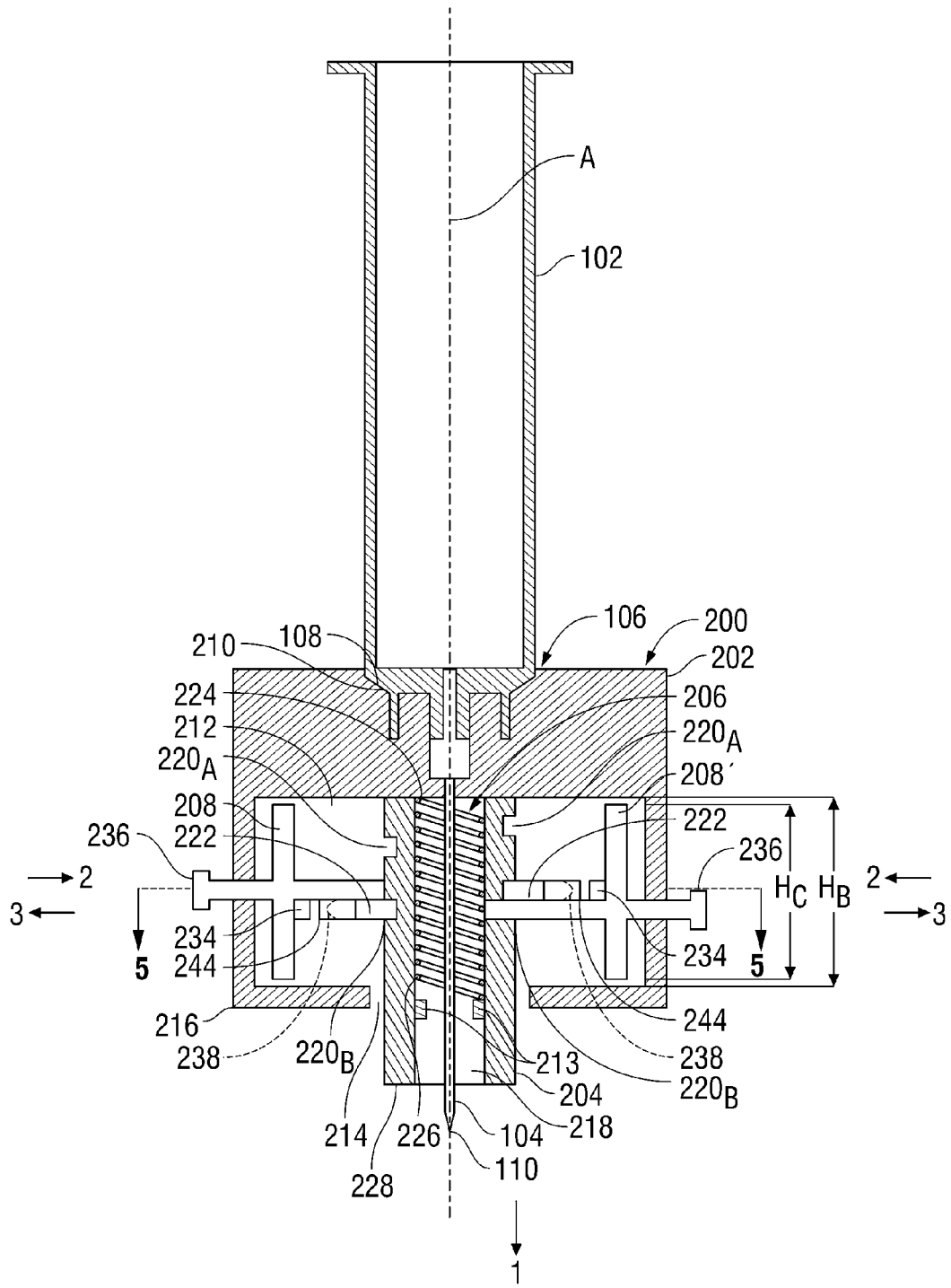
FIG. 2 is a side, cross-sectional view of the safety needle of FIG. 1 illustrating the safety mechanism prior to actuation and showing the shield member in a retracted position.
Figure 3:
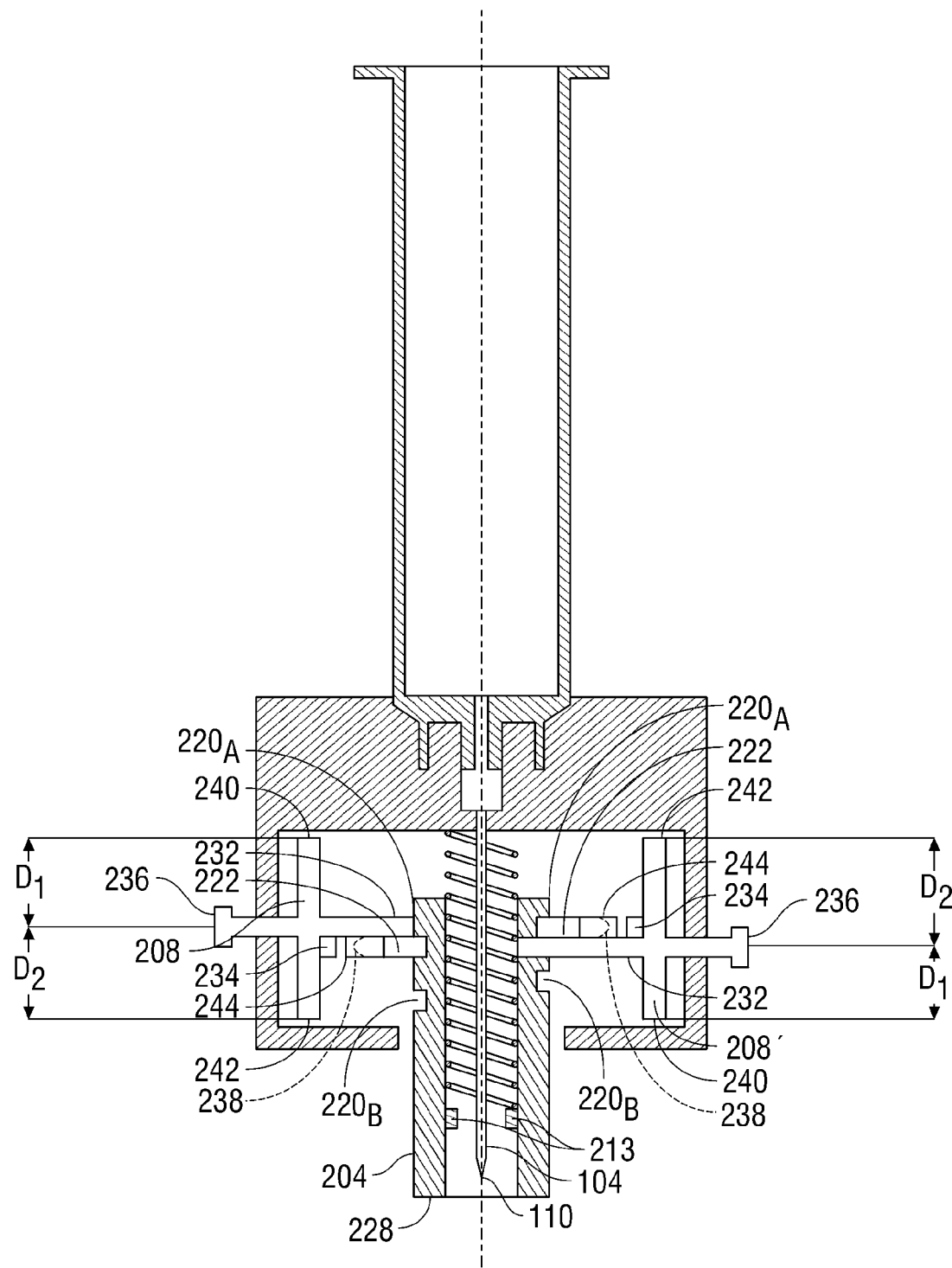
FIG. 3 is a side, cross-sectional view of the safety needle of FIG. 1 illustrating the safety mechanism subsequent to actuation and showing the shield member in an advanced position.

Referring also to FIGS. 2-3, the safety mechanism 200 includes a housing 202, a shield member 204, a biasing member 206, and two identical locking members 208, 208'. The housing 202 defines an internal cavity 212 that accommodates the components of the safety mechanism 200, i.e., the shield member 204, the biasing member 206, and the locking members 208, 208', and includes an opening 214 at the distal end 216 thereof that is configured and dimensioned to allow for passage of the shield member 204. The housing 202 is positioned at a distal end 106 of the syringe 102, and may be releasably connectable with the syringe 102 or fixedly secured thereto. In the embodiment of the safety mechanism 200 seen in FIGS. 2-3, for example, the housing 202 includes receipt structure 210 corresponding in configuration and dimensions to attachment structure 108 formed at the distal end 106 of the syringe 102 such that the safety mechanism 200 may be secured to and disconnected from the syringe 102 after use. While the receipt structure 210 and the attachment structure 108 are illustrated as luer-type connections, any structure suitable for the intended purpose of establishing a releasable connection between the syringe 102 and the housing 202 may be utilized, including but not limited to an interference-fit arrangement or threading.

Referring still to FIGS. 2-3, the shield member 204 is an elongate tubular member defining a passageway 218 therethrough that is configured and dimensioned to receive the biasing member 206 such that the shield member 204 is coaxially positioned about the biasing member 206. In one embodiment of the safety mechanism 200, the shield member 204 includes a proximal pair of apertures 220a and a distal pair of apertures 220b that are spaced longitudinally from each other along the length of the shield member 204. The apertures 220a, 220b are each configured and dimensioned to receive a pair of detents 222 (FIG. 4) included on the locking members 208, 208'. While the apertures 220a, 220b are illustrated as extending only partially through the shield member 204, the apertures 220a, 220b may alternatively extend completely through the shield member 204.

A proximal end 224 of the biasing member 206 abuts the housing 202 such that the biasing member 206 is at least partially positioned within the cavity 212. The biasing member 206 extends distally through the cavity 212 within the shield member 204. A distal end of the biasing member 206 engages a flange 213 formed within the shield member 204 to urge the shield member 204 in a distal direction about the needle 104.

In the embodiment of the safety mechanism 200 seen in FIGS. 2-3, for example, the biasing member 206 is configured as a coil spring 226. However, in alternate embodiments, the biasing member 206 may be any member or structure that is capable of transitioning between a compressed state, seen in FIG. 2, and an expanded state, seen in FIG. 3.

As the biasing member 206 transitions from the compressed state to the expanded state, the biasing member 206 elongates axially in the direction indicated by arrow 1 in FIG. 2, i.e., along the longitudinal axis "A" (FIG. 1). As the biasing member 206 elongates, engagement between the biasing member 206 and the flange 213 of the shield member 204 facilitates movement of the shield member 204 from a retracted position, seen in FIG. 2, to an advanced position, seen in FIG. 3. In the retracted position, the detents 222 (FIG. 4) of the locking members 208, 208' are received by the distal pair of apertures 220b to retain the shield member 204 in the retracted position, and the distal end 110 of the needle 104 extends distally beyond the distal end 228 of the shield member 204 to allow for the penetration of tissue (FIG. 2). By contrast, when the shield member 204 is in the advanced position, the detents 222 of the locking members 208, 208' are received by the proximal pair of apertures 220a to retain the shield member 204 in the advanced position, and the distal end 110 of the needle 104 is concealed by the distal end 228 of the shield member 204 to prevent potentially hazardous or inadvertent contact therewith (FIG. 3).

With additional reference to FIGS. 4 and 4A, the locking members 208, 208' will be described. As previously indicated, the locking members 208, 208' are identical in their configuration and dimensions. Including two identical locking members 208, 208' allows for a substantial reduction in manufacturing costs, e.g., tooling costs, in that the total number of parts requiring fabrication is reduced by one. As the locking members 208, 208' are identical, in the interests of brevity, only the structure of the locking member 208 will be described.

The locking member 208 includes a base 230, an arm 232, and a stop 234. In one embodiment of the locking mechanism 200, the base 230 includes an outwardly extending tactile member 236 that is adapted for manual engagement by the practitioner during use, as seen in FIGS. 1-3, for example. The base 230 defines a height "$H_B$" (FIG. 2) that substantially approximates an internal height "$H_C$" of the cavity 212 defined in the housing 202 such that axial displacement of the locking members 208, 208' within the housing 202, i.e., along the longitudinal axis "A", is substantially prevented.

The arm 232 extends from the base 230 in a substantially parabolic configuration to define a crest 238. The arm 232 includes a pair of resilient biasing members, configured as fingers 244 in the illustrated embodiment, that are configured and dimensioned to engage the stop 234 formed on a corresponding locking member 208' during use, as described in further detail below. The arm 232 may be formed from any suitable material that is at least semi-resilient in nature so as to attribute the requisite measure of resiliency to the fingers 244. Alternatively, only fingers 244 may be formed of a resilient material. Further, fingers 244 can be integrally formed with the arm 232 (FIG. 4) or attached to the arm 232 using any suitable method of attachment, e.g., adhesives, pins, screws, etc. The arm 232 further includes the aforementioned detent 222, which is configured and dimensioned for receipt by the apertures 220a, 220b (FIGS. 2-3) formed in the shield member 204.

In one embodiment of the safety mechanism 200, as seen in FIGS. 2-7, the arm 232 extends eccentrically from the base 230 such that the arm 232 is positioned closer to one end of the base 230 than the other. However, an alternate embodiment of the safety mechanism 200 in which the arm 232 extends from the base 230 such that the arm 232 is positioned equidistant from each end is also within the scope of the present disclosure. With reference to FIG. 3 in particular, in the illustrated embodiment of the safety mechanism 200, the arm 232 is positioned a first distance "$D_1$" from a first end 240 of the base 230 and a second, greater distance "$D_2$" from a second end 242 of the base 230. The difference between the distances "$D_1$" and "$D_2$" is approximately equivalent to the width "W" defined by the arm 232 to facilitate relative positioning of the locking members 208, 208' as illustrated. Specifically, the eccentric configuration of the arm 232 with respect to the base 230 allows one of the locking members, i.e., locking member 208' in the illustrated example, to be inverted such that the arm 232 of the locking member 208 is positionable on top of the arm 232 of the locking member 208'. Accordingly, the first end 240 of the base 230 of the locking member 208 is positioned proximally of the second end 242, whereas the first end 240 of the base 230 of the locking member 208' is positioned distally of the second end 242.

Figure 4:
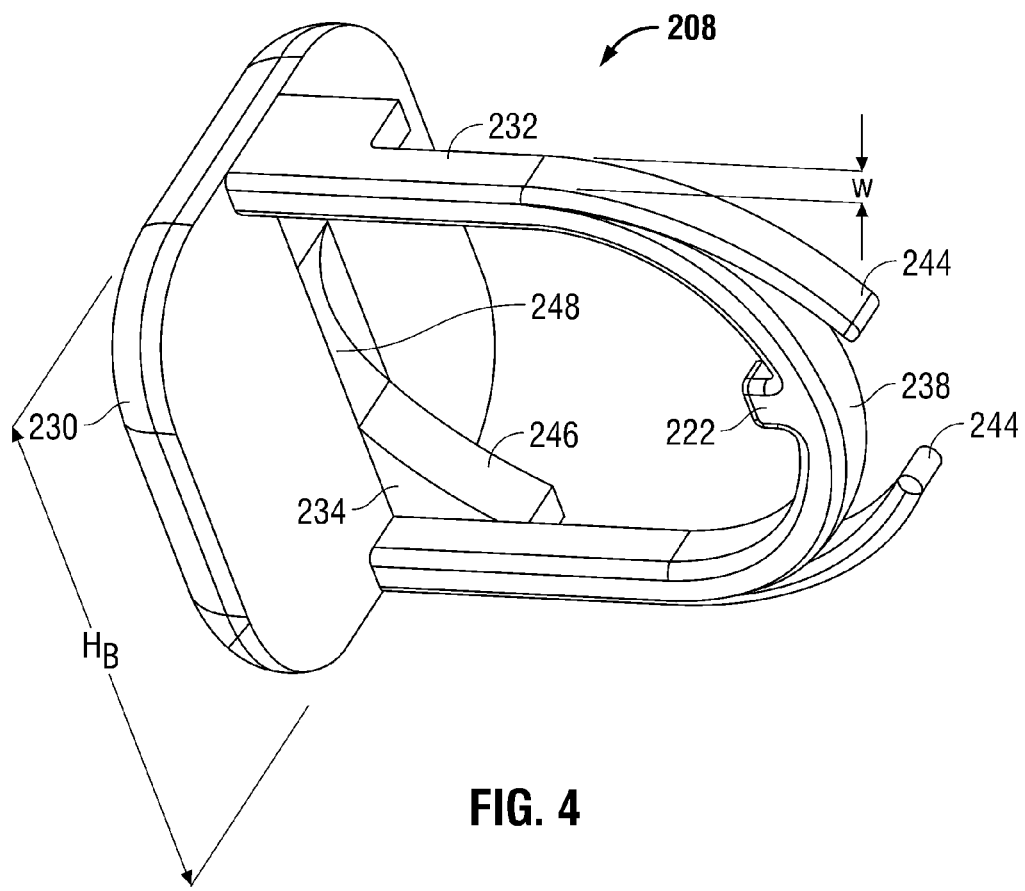
FIG. 4 is a side, perspective view of one of the locking members of the safety mechanism.
Figure 4A:
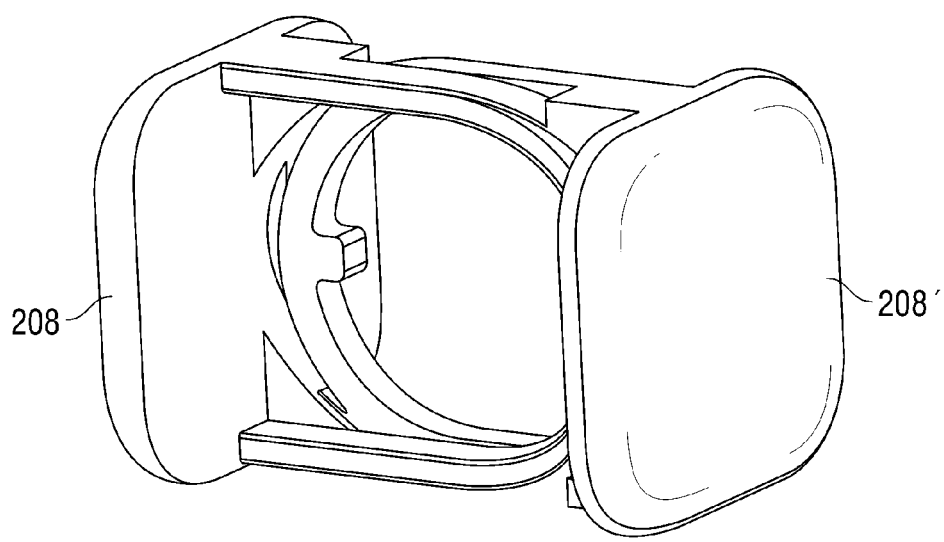
FIG. 4A is a side, perspective view of the pair of locking members seen in FIG. 1 removed from the housing.

As best seen in FIG. 4, the stop 234 extends from the base 230 towards the crest 238 of the arm 232. The stop 234 includes an arcuate surface 246 that defines a well 248 extending into the base 230. The arcuate surface 246 of stop 234 is configured and dimensioned to engage the resilient fingers 244 formed on the arm 232.

Figure 5:
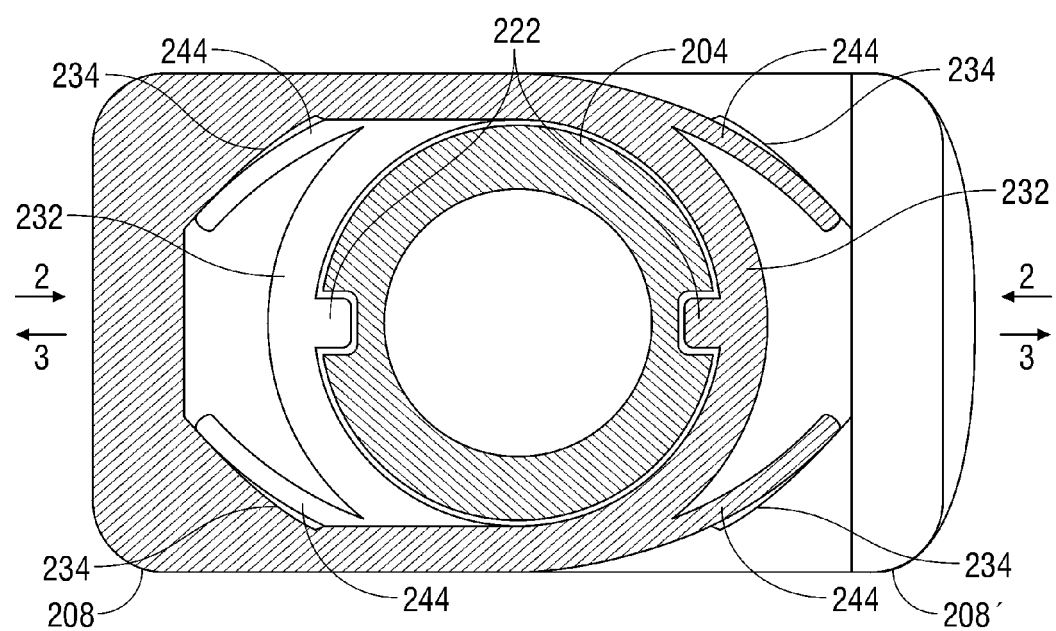
FIG. 5 is a cross-sectional view taken through line 5-5 in FIG. 2 illustrating the safety mechanism prior to actuation with the locking members in a locked position.
Figure 6:
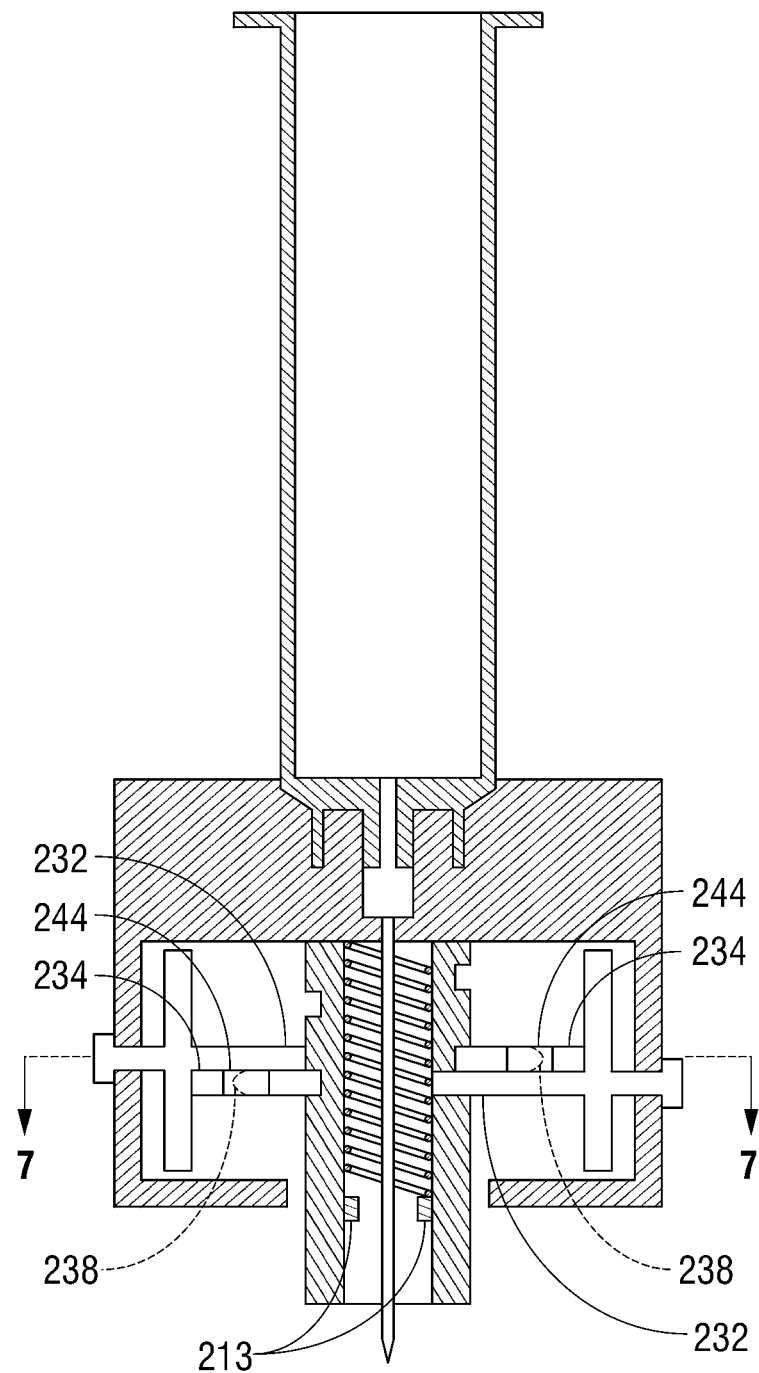
FIG. 6 is a side, cross-sectional view of the safety needle of FIG. 1 illustrating the safety mechanism subsequent to actuation and immediately prior to movement of the shield member into the advanced position.
Figure 7:
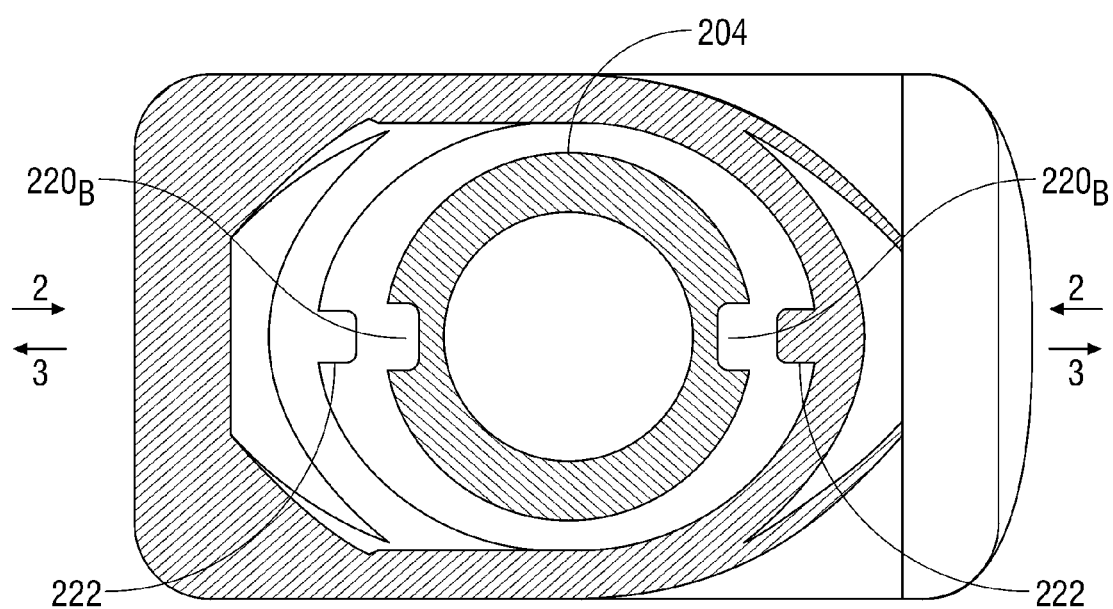
FIG. 7 is a cross-sectional view taken through line 7-7 in FIG. 6 illustrating the safety mechanism immediately subsequent to actuation with the locking members in a release position.

Referring now to FIGS. 2-7, the locking members 208, 208' are positioned within the cavity 212 defined by the housing 202, and are movable upon actuation of the safety mechanism 200 between a locked position, seen in FIGS. 2-3 and 5, and a release position, seen in FIGS. 6-7. In the locked position, the detents 222 extend into the apertures of the shield member 204, i.e., apertures 220a, 220b, to thereby prevent axial displacement of the shield member 204 along the longitudinal axis "A", e.g., from the retracted position seen in FIG. 2 to the advanced position seen in FIG. 3. As the locking members 208, 208' are moved radially inward from the locked position towards the release position, i.e., in the direction indicated by arrows 2 (FIGS. 2, 5, 7), the detents 222 are moved radially outward, i.e., in the direction indicated by arrows 3. Additionally, as the locking members 208, 208' are moved from the locked position towards the release position, the fingers 244 of the locking member 208 are forced into engagement with the stop 234 of the locking member 208', and the fingers 244 of the locking member 208' are forced into engagement with the stop 234 of the locking member 208. As the locking members 208, 208' are continually advanced towards each other, the fingers 244 traverse the arcuate surface 246 of the stops 234 and are deflected towards the crests 238 (FIG. 4) defined by the arms 232, thereby creating a biasing force in the fingers 244 that urges the locking members 208, 208' apart.

In the release position, the fingers 244 are in substantial abutment with both the stops 234 and the crest 238 defined by the arm 232 such that further movement of the fingers 244 is prohibited, as seen in FIG. 6. Additionally, the detents 222 are removed from the apertures 220b in the shield member 204, as seen in FIG. 7, thereby allowing for axial displacement of the shield member 204 from the retracted position to the advanced position.

Referring now to FIGS. 1-7, the use and function of the needle assembly 100 will be described. Prior to use of the needle assembly 100, the biasing member 206 is in the compressed state (FIG. 2), and consequently, the shield member 204 is in the retracted position. Additionally, the locking members 208, 208' are initially in the locked position such that the detents 222 are in engagement with the distal apertures 220b formed in the shield member 204. The engagement of the detents 222 with the distal apertures 220b prevents distal advancement of the shield member 204, thus maintaining the shield member in the retracted position and facilitating the penetration of tissue with the needle 104.

After the safety needle 1000 has served its desired purpose, the practitioner applies a force to the tactile members 236 that is directed radially inward, i.e., in the direction of arrows 2 (FIGS. 2, 5, 7), thereby advancing the locking members 208, 208' towards each other and into the release position seen in FIG. 6. As the locking members 208, 208' move radially inward, the detents 222 move radially outward, i.e., in the direction of arrows 3 (FIGS. 2, 5, 7), such that the detents 222 are displaced from the distal apertures 220b, thereby allowing the biasing member 206 to expand axially in the direction of arrow 1 (FIG. 2). Additionally, as the locking members 208, 208' move radially inward, the fingers 244 engage the stops 234 and are deflected towards the crest 238 (FIG. 4) of the arm 232, thus creating a biasing force that urges the locking members 208, 208' apart and into the locked position.

As the biasing member 206 expands axially, the shield member 204 is displaced distally into the advanced position seen in FIG. 3 to conceal the needle 104. Subsequently, the practitioner can release the tactile members 236, thereby allowing the biasing force in the fingers 244 to urge the locking members 208, 208' radially outward in the direction of arrows 3 (FIGS. 2, 5, 7). As the locking members 208, 208' move radially outward, the detents 222 move radially inward in the direction of arrows 2 and into engagement with the proximal apertures 220a formed in the shield member 204. The engagement of the detents 222 with the proximal apertures 220a prevents proximal displacement of the shield member 204, thus maintaining the advanced position of the shield member 204 and preventing inadvertent contact with the needle 104.

Figure 8:
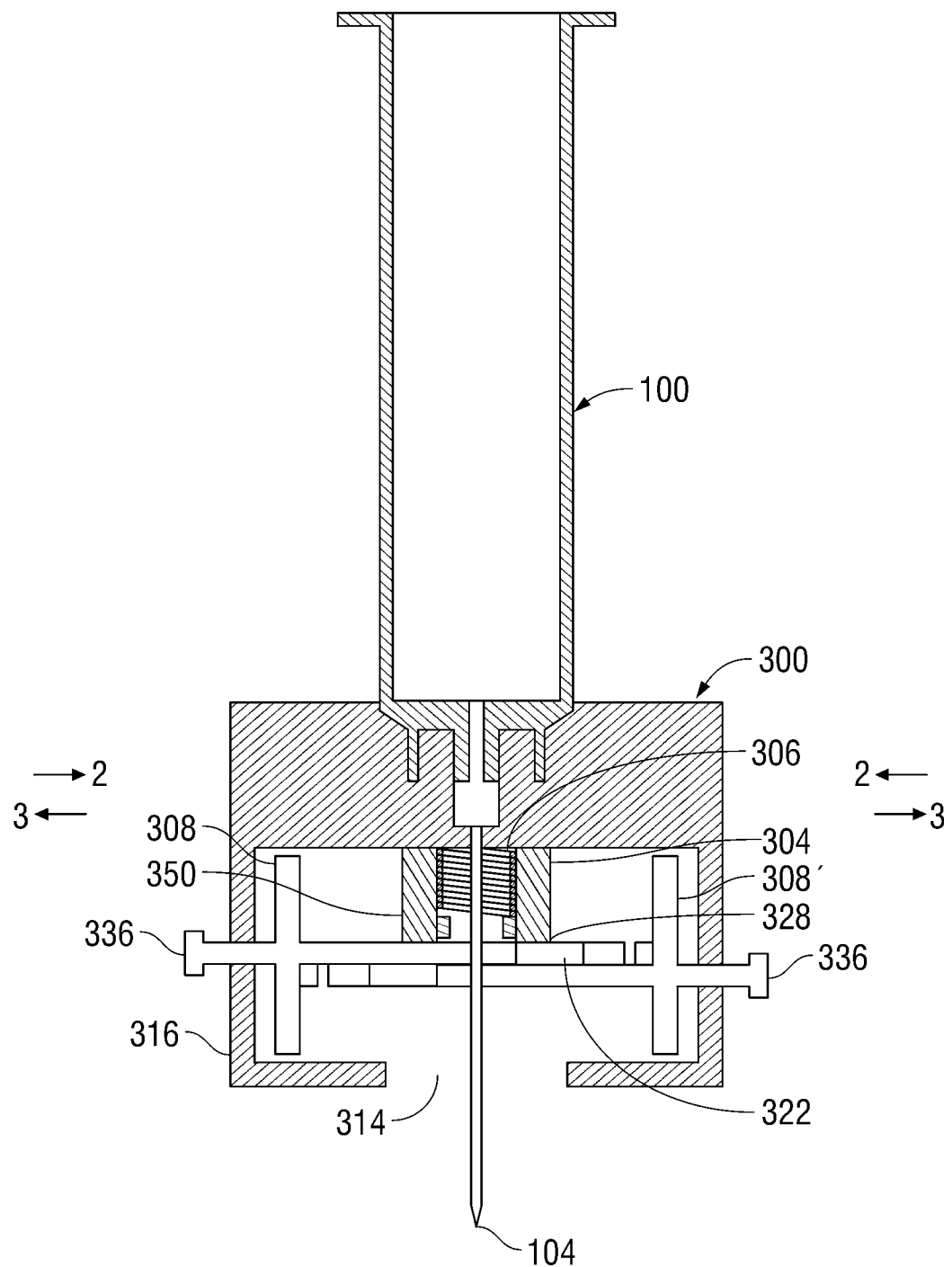
FIG. 8 is a side, cross-sectional view of the safety needle of FIG. 1 including another embodiment of the safety mechanism shown prior to actuation.
Figure 9:
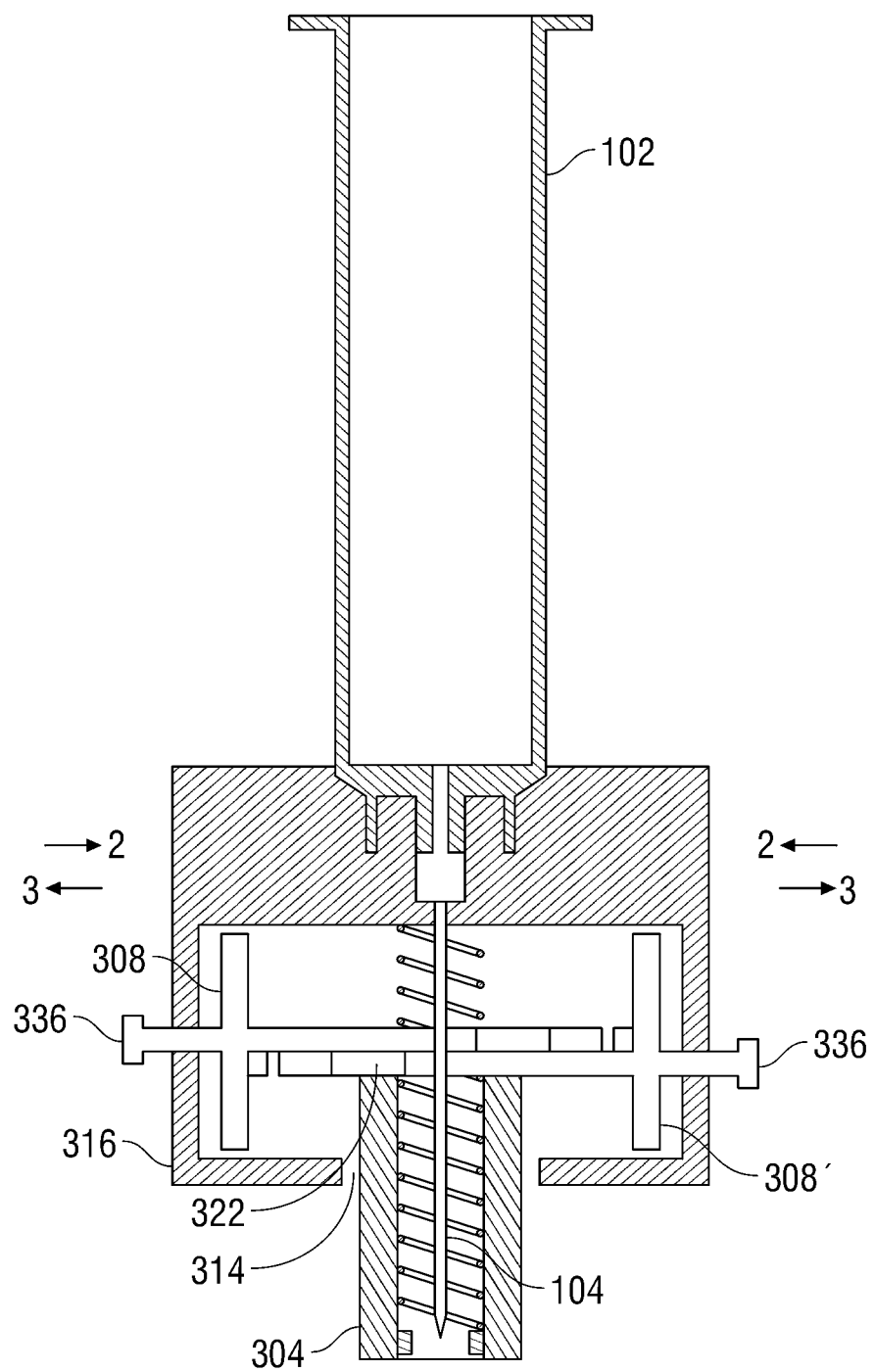
FIG. 9 is a side, cross-sectional view of the safety needle seen in FIG. 8 showing the safety mechanism subsequent to actuation.
Figure 10:
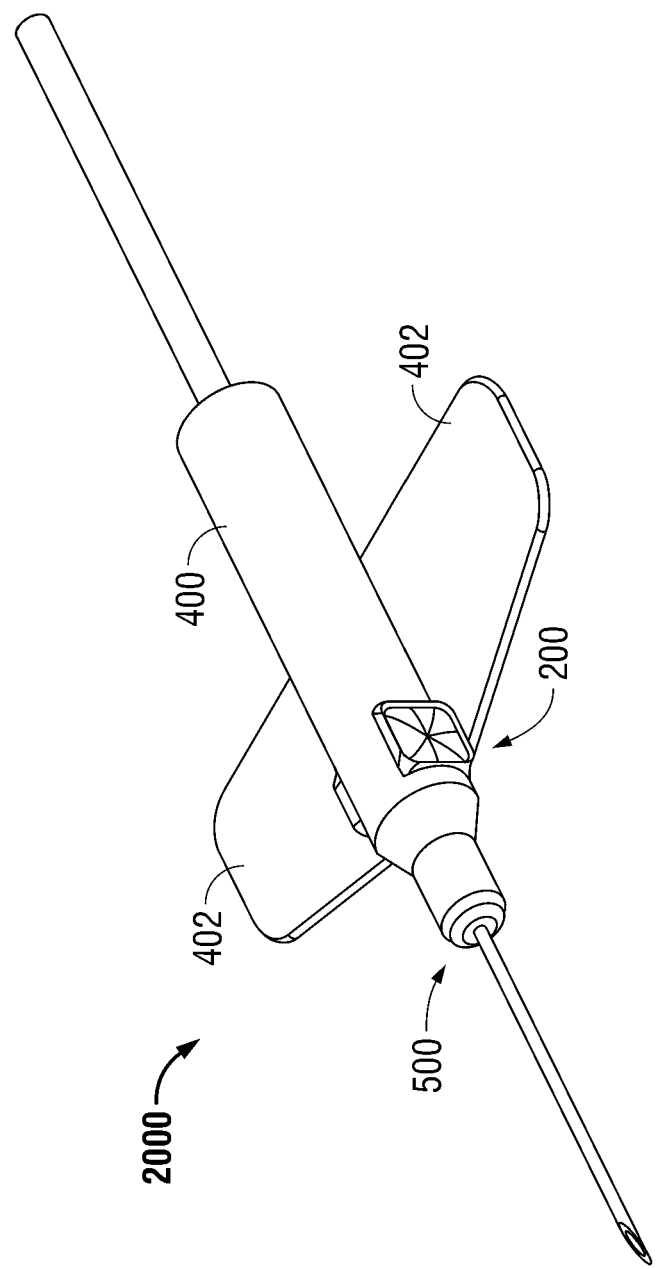
FIG. 10 is a side, perspective view of another embodiment of the safety needle seen in FIG. 1, incorporating a housing portion, a needle assembly, and a safety mechanism.

Referring now to FIGS. 8-9, an alternate embodiment of the safety mechanism, referred to generally as safety mechanism 300, will be discussed in connection with the needle assembly 100 seen in FIG. 1. The safety mechanism 300 is substantially similar to the safety mechanism 200 discussed above with respect to FIGS. 1-7, but for the configuration of the shield member 304, and accordingly, will only be discussed with respect thereto.

In contrast to the shield member 204 of the safety mechanism 200, which includes proximal and distal apertures 220a, 220b, the shield member 304 defines a substantially uniform outer surface 350.

Prior to use, the biasing member 306 is in the compressed state seen in FIG. 8, and consequently, the shield member 304 is in the retracted position. In the retracted position, the distal end 328 of the shield member 304 is positioned proximally of the detent 322 included on the locking member 308 such that the distal end 328 of the shield member 304 rests thereupon. The engagement of the detent 322 with the distal end 328 of the shield member 304 prevents distal displacement the shield member 304, thus maintaining the retracted position of the shield member 304 and facilitating the penetration of tissue with the needle 104.

Following use, the practitioner actuates the safety mechanism 300 by engaging the tactile members 336 and advancing the locking members 308, 308' radially inward in the direction of arrows 2 and into the release position. As the locking members 308, 308' move radially inward, the detents 322 move radially outward in the direction of arrows 3 and out of engagement with the distal end 328 of the shield member 304 such that the shield member 304 is allowed to advance distally between the detents 322, through the locking members 308, 308' and the opening 314 at the distal end 316 of the housing 302, and into the advanced position seen in FIG. 9. Thereafter, the practitioner can release the tactile members 336, thus allowing the locking members 308, 308' to return to the locked position, as described above. In the locked position, the detents 322 prevent proximal displacement of the shield member 304, thus maintaining the advanced position of the shield member 304 and preventing inadvertent contact with the needle 104.

With reference now to FIGS. 10-14, an alternate embodiment of the safety needle, referred to generally by reference character 2000, will be discussed. The safety needle 2000 is suitable for use in a variety of surgical procedures requiring the infusion, injection, or withdrawal of fluids from the body of a patient. The safety needle 2000 includes a housing portion 400, a needle assembly 500, and the safety mechanism 200 discussed above with respect to FIGS. 1-7.

Figure 11:
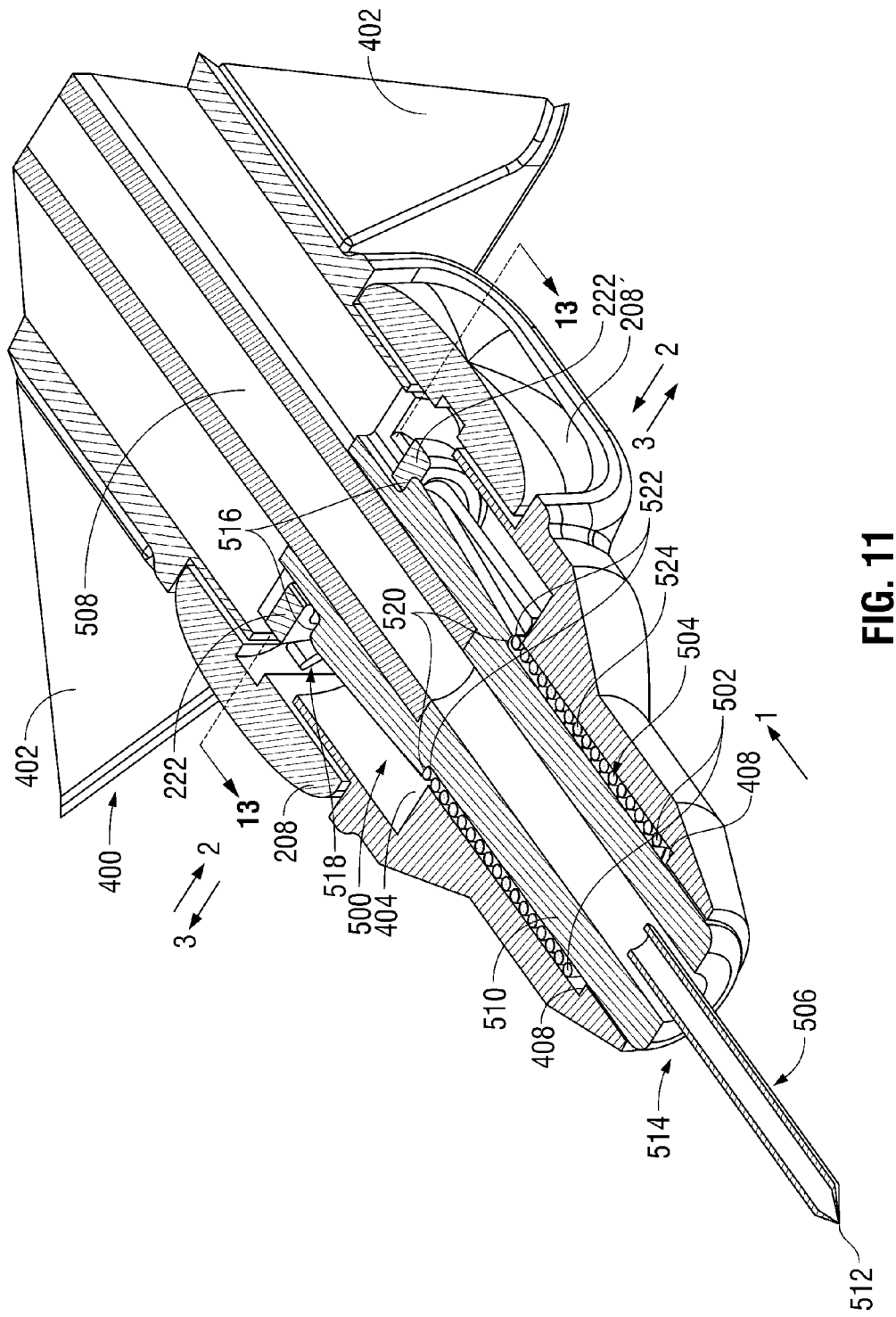
FIG. 11 is a partial, longitudinal cross-sectional view of the safety needle of FIG. 10 illustrating the safety mechanism prior to actuation.
Figure 12:
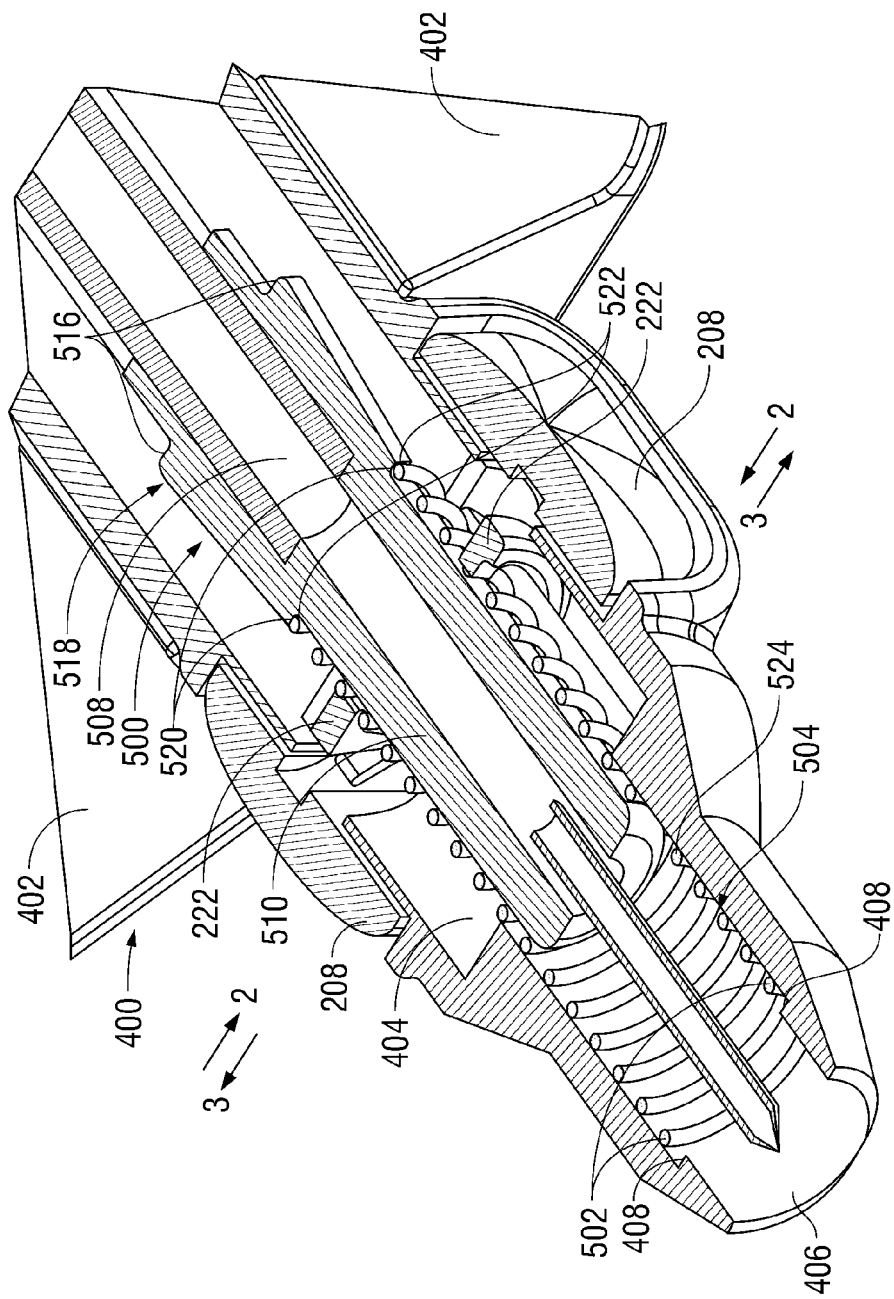
FIG. 12 is a partial, longitudinal cross-sectional view of the safety needle of FIG. 10 illustrating the safety mechanism subsequent to actuation.

Referring now to FIGS. 11-12 in particular, the housing portion 400 includes one or more wings 402 to stabilize the safety needle 2000 with respect to a patient, e.g., with respect to a patient's arm, by providing an attachment point for tape, or any other such securing means. Wings 402 provide structure for grasping the safety needle 20000 as known in the art. The housing portion 400 defines an internal cavity 404 that is configured and dimensioned to accommodate movement of the needle assembly 500 between retracted and advanced positions, as will be described below, as well as the components of the safety mechanism 200. The housing portion 400 includes a distal opening 406 (FIG. 12) that allows the needle assembly 500 to extend therethrough. An internal ridge 408 is recessed within the distal opening 406 and is configured to engage a distal end 502 of a biasing member 504. Although illustrated in an abutting relationship, the distal end 502 of the biasing member 504 may be fixedly secured to the housing portion 400 at the internal ridge 408.

The needle assembly 500 includes an elongate, hollow needle 506, tubing 508, a hub member 510, and the aforementioned biasing member 504. The needle 506 is of the type typically used during intravenous procedures to insert and withdraw fluids from the body, and includes a distal tip 512 that is adapted to penetrate tissue. The needle 506 is in fluid communication with the tubing 508 to facilitate the passage of fluid into and out of the body through the needle 506.

The hub member 510 is positioned within the internal cavity 404 defined by the housing portion 400. A distal end 514 of the hub member 510 is fixedly secured to the needle 506. The hub member 510 and the needle 506 may be secured together in any suitable manner, e.g., crimping, adhesives, press-fitting, etc. The hub member 510 includes a ledge 516 formed at a proximal end 518 that is configured and dimensioned to engage the detents 222 of the locking members 208, 208', which can also be seen in FIGS. 4 and 4A. While the ledge 516 is illustrated as extending only partially through the hub member 510, the ledge 516 may alternatively extend completely through the hub member 510 to define an aperture or other such opening. The hub member 510 further includes a ridge, or step 520 positioned distally of the ledge 516 that is configured and dimensioned to engage a proximal end 522 of the biasing member 504. Although illustrated in an abutting relationship, the proximal end 522 of the biasing member 504 maybe fixedly secured to the hub member 510 at the ridge 520. In the embodiment of the safety needle 2000 seen in FIGS. 11-12, for example, the biasing member 504 is configured as a coil spring 524 that is positioned coaxially about the hub member 510. However, in alternative embodiments of the safety needle 2000, it is envisioned that the biasing member 504 may be any member or structure that is capable of transitioning between a compressed state, seen in FIG. 11, and an expanded state, seen in FIG. 12.

As the biasing member 504 transitions from the compressed state to the expanded state, the biasing member 504 elongates axially in the proximal direction indicated by arrow 1 (FIG. 11). Distal movement of the biasing member 504 is substantially restricted through the engagement of the distal end 502 of the biasing member 504 with the internal ridge 408 of the housing portion 400. As the biasing member 504 elongates proximally, the hub member 510 will be forced proximally in the direction of arrow 1 due to the engagement between the proximal end 522 of the biasing member 504 and the ridge 520 formed on the hub member 510, to thereby reposition the needle assembly 500 from an advanced position, seen in FIG. 11, to a retracted position, seen in FIG. 12. When the needle assembly 500 is in the advanced position, the needle 506 extends distally beyond the housing portion 400 to facilitate the penetration of tissue with the needle 506, and when the needle assembly 500 is in the retracted position, the needle 506 is positioned within the housing portion 400 to prevent inadvertent contact with the needle 506. The advanced position of the needle assembly 500 is maintained until actuation of the safety mechanism 200 by the practitioner through the engagement of the ledge 516 formed at the proximal end 518 of the hub member 510 with the detents 222 of the locking members 208, 208'.

Figure 13:
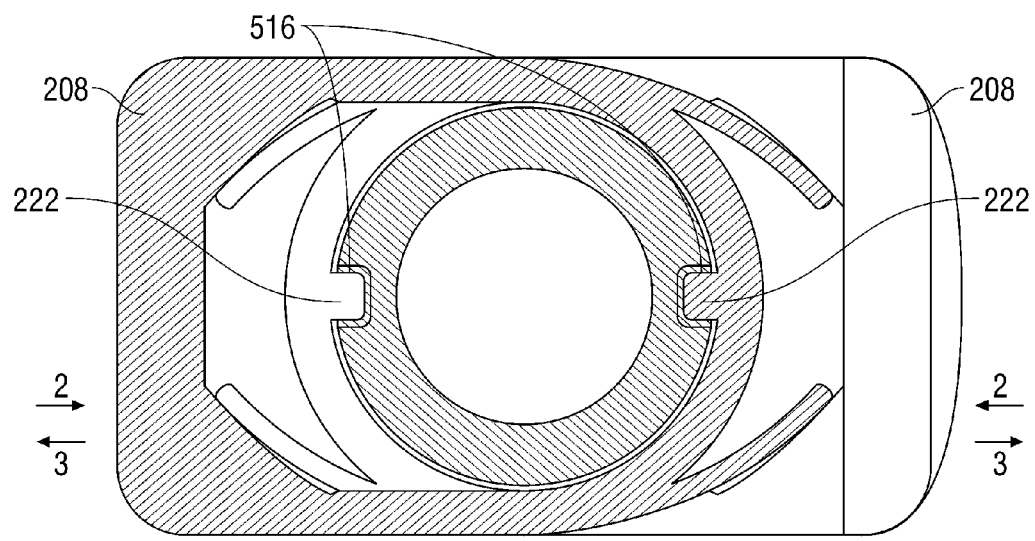
FIG. 13 is a cross-sectional view taken through line 13-13 in FIG. 11 illustrating the safety mechanism prior to actuation with a pair of locking members in a locked position.
Figure 14:
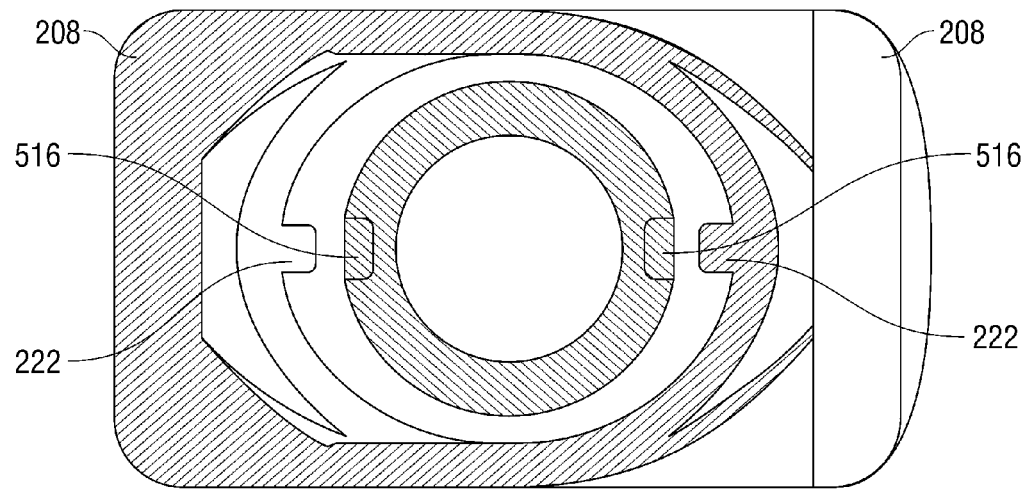
FIG. 14 is a cross-sectional view also taken through line 13-13 in FIG. 11 illustrating the safety mechanism immediately subsequent to actuation with the pair of locking members in a release position.

As previously discussed with respect to FIGS. 2-7, upon actuation of the safety mechanism 500, the locking members 208, 208' are moved from a locked position, seen in FIGS. 11 and 13, to a release position, seen in FIGS. 12 and 14. In the locked position, the detents 222 engage the ledge 516 to prevent axial displacement of the hub member 510 from the advanced position seen in FIG. 11 to the retracted position seen in FIG. 12. However, as the locking members 208, 208' are moved radially inward from the locked position towards the release position, i.e., in the direction indicated by arrows 2 (FIGS. 11 and 13), the detents 222 are moved radially outward, i.e., in the direction indicated by arrows 3, and out of engagement with the ledge 516 (FIG. 14), thereby allowing for proximal, axial displacement of the hub member 510, and thus, movement of the needle assembly 500 from the advanced position into the retracted position. It is envisioned that the hub member 510 can include a distal ledge, step, or recess which is positioned to receive detents 222 when the hub member 510 is in the retracted position to retain the hub member in the retracted position.

Persons skilled in the art will understand that the devices and methods specifically described herein and illustrated in the accompanying drawings are intended to be construed as non-limiting, exemplary embodiments, and that the features illustrated or described in connection with one exemplary embodiment may be combined with the features of other embodiments. Additionally, one skilled in the art will appreciate further features and advantages of the disclosure based on the above-described embodiments. Accordingly, the disclosure is not to be limited by what has been particularly shown and described, except as indicated by the appended claims.

What is claimed is:

1. A safety device assembly comprising:
  a medical device having a sharp element; and
  a safety mechanism positioned at a distal end of the medical device in association with the sharp element, the safety mechanism including:
    a housing defining an internal cavity;
    a shield member at least partially disposed within the internal cavity; and
    first and second locking members configured to selectively engage the shield member to maintain the shield member in one or more predetermined positions, the first and second locking members being movable between a locked position, in which the first and second locking members are in engagement with the shield member to substantially prevent axial movement thereof, and a release position, in which the first and second locking members are disengaged from the shield member to permit axial movement of the shield member to cover the sharp element, wherein the first and second locking members are discrete structures, and each include a biasing member, the biasing member of each locking member being positioned to cooperate with the other of the first and second locking members to normally bias the locking members towards the locked position.

2. A safety needle assembly comprising:
  a syringe; and
  a safety mechanism positioned at a distal end of the syringe, the safety mechanism including:
    a housing defining an internal cavity;
    a shield member at least partially disposed within the internal cavity; and
    first and second locking members configured to selectively engage the shield member to maintain the shield member in one or more predetermined positions, the first and second locking members being movable between a locked position, in which the first and second locking members are in engagement with the shield member to substantially prevent axial movement thereof, and a release position, in which the first and second locking members are disengaged from the shield member to permit axial movement of the shield member, wherein the first and second locking members are discrete structures, and each include a biasing member, the biasing member of each locking member being positioned to cooperate with the other of the first and second locking members to normally bias the locking members towards the locked position.

3. The safety needle assembly of claim 2, wherein the first and second locking members define substantially identical configurations and dimensions.

4. The safety needle assembly of claim 2, wherein the first and second locking members are adapted for reciprocal movement between the locked position and the release position.

5. The safety needle assembly of claim 2, wherein the first and second locking members each include a tactile member configured for manual engagement to facilitate movement of the first and second locking members from the locked position to the release position.

6. The safety needle assembly of claim 4, wherein the biasing member of the first locking member includes a first resilient finger and the biasing member of the second locking member includes a second resilient finger.

7. The safety needle assembly of claim 6, wherein first locking member includes a first stop and the first resilient finger, and the second locking member includes a second stop and the second resilient finger, the first resilient finger being configured and dimensioned for engagement with the second stop and the second resilient finger being configured and dimensioned for engagement with the first stop to normally bias the first and second locking members towards the locked position.

8. The safety needle assembly of claim 7, wherein the shield member is movable between retracted and advanced positions.

9. The safety needle assembly of claim 8, further including a needle extending distally from the syringe.

10. The safety needle assembly of claim 9, wherein a distal end of the needle extends distally beyond a distal end of the shield member when the shield member is in the retracted position, and wherein the distal end of the shield member extends distally beyond the distal end of the needle when the shield member is in the advanced position.

11. The safety needle assembly of claim 8, wherein the shield member passes through the first and second locking members as the shield member moves between the retracted and advanced positions.

12. The safety needle assembly of claim 8, wherein the housing includes an opening at a distal end thereof that is configured and dimensioned to allow the shield member to pass therethrough as the shield member moves from the retracted position to the advanced position.

13. The safety needle assembly of claim 8, further including a biasing member engagable with the shield member to normally bias the shield member towards the advanced position.

14. The safety needle assembly of claim 8, further including a biasing member engagable with the shield member to normally bias the shield member towards the retracted position.

15. The safety needle assembly of claim 12, wherein the first locking member includes a first detent and the second locking member includes a second detent.

16. The safety needle assembly of claim 15, wherein the shield member includes at least one aperture that is configured and dimensioned to engage the first and second detents.

17. The safety needle assembly of claim 16, wherein the first and second detents are positioned within the at least one aperture when the first and second locking members are in the locked position and displaced therefrom when the first and second locking members are in the release position.

18. The safety needle assembly of claim 17, wherein the at least one aperture includes a proximal pair of apertures and a distal pair of apertures, the first and second detents being positionable within the distal pair of apertures to maintain the retracted position of the shield member and positionable within the proximal pair of apertures to maintain the advanced position of the shield member.

19. The safety needle assembly of claim 18, wherein the first and second locking members are displaced radially inward with respect to a longitudinal axis of the housing as the first and second locking members move from the locked position to the release position.

20. The safety needle assembly of claim 16, wherein the first detent is positioned on a first arm of the first locking member and the second detent is positioned on a second arm of the second locking member such that the first and second detents are displaced radially outward and out of engagement with the at least one aperture as the first and second locking members are displaced radially inward, thereby permitting the shield member to move from the retracted position to the advanced position.

21. The safety needle assembly of claim 20, wherein the distal end of the shield member is engagable with the first detent to maintain the retracted position of the shield member.

22. The safety needle assembly of claim 21, wherein a proximal end of the shield member is engagable with the second detent to maintain the advanced position of the shield member.

23. A safety mechanism adapted for use with a medical device, the safety mechanism comprising:
 a housing defining an internal cavity;
 a shield member at least partially disposed within the internal cavity; and
 first and second locking members configured and dimensioned to selectively engage the shield member to maintain the shield member in one or more predetermined positions, wherein the first and second locking members are movable between a locked position, in which the first and second locking members are in engagement with the shield member to substantially prevent axial movement thereof, and a release position, in which the first and second locking members are disengaged from the shield member to permit axial movement of the shield member, wherein the first and second locking members are discrete structures, and each include a biasing member, the biasing member of each locking member being positioned to cooperate with the other of the first and second locking members to normally bias the locking members towards the locked position.

24. The safety mechanism of claim 23, wherein the first and second locking members define substantially identical configurations and dimensions.

25. The safety mechanism of claim 23, wherein first locking member includes a first stop and the first resilient finger, and the second locking member includes a second stop and the second resilient finger, the first resilient finger being configured and dimensioned for engagement with the second stop and the second resilient finger being configured and dimensioned for engagement with the first stop to normally bias the first and second locking members towards the locked position.

26. The safety device of claim 1, wherein the biasing member of the first locking member is engagable with the second locking member, and the biasing member of the second locking member is engagable with the first locking member.

27. The safety needle assembly of claim 2, wherein the biasing member of the first locking member is engagable with the second locking member, and the biasing member of the second locking member is engagable with the first locking member.

28. The safety mechanism of claim 23, wherein the biasing member of the first locking member is engagable with the second locking member, and the biasing member of the second locking member is engagable with the first locking member.

* * * * *